United States Patent
Baichwal

(10) Patent No.: US 6,245,355 B1
(45) Date of Patent: Jun. 12, 2001

(54) SUSTAINED RELEASE MATRIX FOR HIGH-DOSE INSOLUBLE DRUGS

(75) Inventor: Anand R. Baichwal, Wappingers Falls, NY (US)

(73) Assignee: Edward Mendell Co., Inc., Patterson, NY (US)

( * ) Notice: Subject to any disclaimer, the term of this patent is extended or adjusted under 35 U.S.C. 154(b) by 0 days.

(21) Appl. No.: 09/420,247

(22) Filed: Oct. 19, 1999

Related U.S. Application Data

(63) Continuation of application No. 08/889,424, filed on Jul. 8, 1997.
(60) Provisional application No. 60/021,335, filed on Jul. 8, 1996.

(51) Int. Cl.⁷ ............................. A61K 9/20; A61K 31/19; A61K 9/22
(52) U.S. Cl. .................................... 424/468; 424/464
(58) Field of Search ................... 424/468, 465; 514/568

(56) References Cited

U.S. PATENT DOCUMENTS

| | | | |
|---|---|---|---|
| 3,485,847 | 12/1969 | Bossert et al. | 260/295.5 |
| 3,784,684 | 1/1974 | Bossert et al. | 424/37 |
| 4,191,772 | 3/1980 | Woog et al. | 424/273 R |
| 4,346,709 | 8/1982 | Schmitt | 128/260 |
| 4,412,986 | 11/1983 | Kawata et al. | 424/80 |
| 4,562,069 | 12/1985 | Hegasy et al. | 424/80 |
| 4,665,081 | 5/1987 | Doi et al. | 514/356 |
| 4,673,564 | 6/1987 | Kawata et al. | 424/494 |
| 4,696,815 | 9/1987 | Schepky et al. | 424/80 |
| 4,764,382 | 8/1988 | Kydonieus et al. | 424/449 |
| 4,765,989 | 8/1988 | Wong et al. | 424/473 |
| 4,765,990 | 8/1988 | Sugimoto et al. | 424/494 |
| 4,792,448 | 12/1988 | Ranade | 424/438 |
| 4,792,450 | 12/1988 | Kydonieus et al. | 424/449 |
| 4,792,452 | 12/1988 | Howard et al. | 424/475 |
| 4,803,076 | 2/1989 | Ranade | 424/438 |
| 4,803,081 | 2/1989 | Falk et al. | 424/488 |
| 4,808,413 | 2/1989 | Joshi et al. | 424/458 |
| 4,851,229 | 7/1989 | Magruder et al. | 424/457 |
| 4,867,985 | 9/1989 | Heafield et al. | 424/461 |
| 4,880,623 | 11/1989 | Piergiorgio et al. | 424/78 |
| 4,889,723 | 12/1989 | Kim et al. | 424/450 |
| 4,892,741 | 1/1990 | Ohm et al. | 424/479 |
| 4,894,235 | 1/1990 | Kohne et al. | 424/452 |
| 4,904,699 | 2/1990 | Bauer | 514/972 |
| 4,940,587 | 7/1990 | Jenkins et al. | 424/480 |
| 4,942,040 | 7/1990 | Ragnarsson et al. | 424/486 |
| 4,973,469 | 11/1990 | Mulligan et al. | 424/461 |
| 4,983,593 | 1/1991 | Miyajima et al. | 514/110 |
| 4,994,276 | 2/1991 | Baichwal et al. | 424/440 |
| 5,007,790 | 4/1991 | Shell | 424/451 |
| 5,015,479 | 5/1991 | Mulligan et al. | 424/457 |
| 5,019,397 | 5/1991 | Wong et al. | 424/473 |
| 5,024,843 | 6/1991 | Kuczynski et al. | 424/499 |
| 5,051,263 | 9/1991 | Barry et al. | 424/490 |
| 5,071,642 | 12/1991 | Lahr et al. | 424/474 |
| 5,091,190 | 2/1992 | Kuczynski et al. | 424/473 |
| 5,096,714 | 3/1992 | Kuhrts | 424/439 |
| 5,100,669 | 3/1992 | Hyon et al. | 424/426 |
| 5,108,757 | 4/1992 | Erdos et al. | 424/451 |
| 5,110,602 | 5/1992 | Kim et al. | 424/451 |
| 5,128,142 | 7/1992 | Mulligan et al. | 424/457 |
| 5,128,143 | 7/1992 | Baichwal et al. | 424/464 |
| 5,132,116 | 7/1992 | Soumac et al. | 424/469 |
| 5,133,974 | 7/1992 | Paradissis et al. | 424/480 |
| 5,135,757 | 8/1992 | Baichwal et al. | 424/465 |
| 5,145,683 | 9/1992 | Rhodes | 424/451 |
| 5,160,734 | 11/1992 | Ganesan et al. | 424/78.38 |
| 5,169,638 | 12/1992 | Dennis et al. | 424/457 |
| 5,169,639 | 12/1992 | Baichwal | 424/468 |
| 5,211,957 | 5/1993 | Hagemann et al. | 424/466 |
| 5,215,758 | 6/1993 | Krishnamurthy | 424/488 |
| 5,264,446 | 11/1993 | Hegasy et al. | 514/356 |

(List continued on next page.)

FOREIGN PATENT DOCUMENTS

| | | | |
|---|---|---|---|
| 1288049 | 8/1991 | (CA) . | |
| 2101680 | 2/1994 | (CA) | A61K/31/44 |
| 2714065 | 10/1978 | (DE) | A61K/9/10 |
| 3400106 | 7/1985 | (DE) | A61K/9/00 |
| 0047899 | 3/1982 | (EP) | A61K/9/14 |
| 0147171 | 7/1985 | (EP) | C07D/401/12 |
| 0234670 | 2/1987 | (EP) . | |
| 0357793 | 3/1990 | (EP) . | |
| 0232155 | 8/1997 | (EP) . | |
| 2160100 | 12/1995 | (GB) | A61K/9/22 |
| 8504100 | 9/1985 | (WO) | A61K/9/40 |
| WO8902738 | 4/1989 | (WO) . | |
| WO9206680 | 4/1992 | (WO) . | |
| 9313773 | 7/1993 | (WO) | A61K/31/44 |
| 9423700 | 10/1994 | (WO) | A61K/9/16 |

OTHER PUBLICATIONS

Chemical Abstracts, vol. 104 (1986) Abstract 174662y.
Chemical Abstracts, vol. 99 (1983) Abstract 128360d.
Chemical Abstracts, vol. 92 (1980) Abstract 135278s.
Chemical Abstracts, vol. 92 (1980) Abstract 82429h.
Chemical Abstracts, vol. 77 (1972) Abstract 39130g.
Chemical Abstracts, vol. 70 (1969) Abstract 17133p.
Chemical Abstracts, vol. 98 (1983) Abstract 221832y.
Alderman, D.A., "A review of cellulose ethers in hydrophilic matrices for oral controlled-release dosage forms", *Int. J. Pharm. Tech. & Prod. Mfg.*, vol. 5, pp. 1–9 (1984).
Haynes, R. Brain, M.D., et al., "Manipulation of the therapeutic regimen to improve compliance: Conceptions and misconceptions", *Clinical Pharmacology and Therapeutics*, vol. 22, No. 2, (Aug. 1977).

(List continued on next page.)

*Primary Examiner*—Thurman K. Page
*Assistant Examiner*—Amy E Pulliam
(74) *Attorney, Agent, or Firm*—Davidson, Davidson & Kappel, LLC

(57) ABSTRACT

Sustained release dosage forms of high dose insoluble drugs such as ibuprofen and methods for their manufacture are disclosed.

8 Claims, 2 Drawing Sheets

U.S. PATENT DOCUMENTS

| | | | |
|---|---|---|---|
| 5,264,459 | 11/1993 | Chelmick-Schorr et al. | 514/646 |
| 5,273,760 | 12/1993 | Ohslack et al. | 424/480 |
| 5,286,493 | 2/1994 | Oshlack et al. | 424/468 |
| 5,288,500 | 2/1994 | Ibsen | 424/489 |
| 5,292,534 | 3/1994 | Valentine et al. | 424/451 |
| 5,330,761 * | 7/1994 | Baichwal | 424/469 |
| 5,356,467 | 10/1994 | Oshlack et al. | 106/153 |
| 5,415,871 | 5/1995 | Pankhania et al. | 424/486 |
| 5,439,687 | 8/1995 | Compassi | 424/468 |
| 5,455,046 | 10/1995 | Baichwal | 424/457 |
| 5,472,711 | 12/1995 | Baichwal | 424/468 |
| 5,476,654 | 12/1995 | Conte et al. | 424/78.08 |
| 5,478,574 | 12/1995 | Baichwal et al. | 424/485 |
| 5,512,297 | 4/1996 | Baichwal | 424/451 |
| 5,518,730 | 5/1996 | Fuisz | 424/426 |
| 5,543,099 | 8/1996 | Zhang et al. | 264/115 |
| 5,554,387 | 9/1996 | Baichwal | 424/488 |
| 5,662,933 | 9/1997 | Baichwal et al. | 424/457 |
| 5,667,801 | 9/1997 | Baichwal | 424/457 |
| 5,670,168 | 9/1997 | Baichwal et al. | 424/464 |
| 5,773,025 | 6/1998 | Baichwal | 424/458 |
| 5,846,563 | 12/1998 | Baichwal | 424/457 |
| 5,958,456 | 9/1999 | Baichwal et al. | 424/489 |

OTHER PUBLICATIONS

English translation of Japanese Patent Laid–Open–To–Public, publication No. 8/1986, publication date Jan. 6, 1986, Japanese Patent Application No. 118,789/1984; Japanese Patent Application date: Jun. 9, 1984.

*Techniques of Solubilization of Drugs*, edited by Samuel H. Yalkowsky, The Upjohn Company, pub. Marcel Dekker, Inc., New York and Basel, pp. 308–315 (1981).

"Crystalliztion and Granulation", Remington's Practice of Pharmacy, 9th Ed. Chapter XXVII, pp. 208–211, 1950.

Ritschel, Angewandte Biopharmazie, pp. 293–302 (1973).

Sugimoto, I., et al., "Dissolution and Absorption of Nifedipine From Nifedipine–Polyvinylpyrrolidone Coprecipitate", *Drug Development and Industrial Pharmacy*, vol. 6, No. 2, pp., 137–161 (1980).

Kleinblosem, M., et al., Nifedipine: Kinetics and dynamics in healthy subjects, *Clin. Pharmacol. Ther.*, Vo. 35, No. 6, pp. 742–749 (1984).

Ramasch, K., et al., "Pharmacokinetics and Metabolism of Nifediphine", *Hypertension Supplement II*, Vo.5, No. 4, Jul.–Aug. 18–24 (1983).

McGinty, J.W., et al., "Dissolution and Uniformity Properties of Ordered Mixes of Micronized Griseofulvin and a Directly Compressible Excipient", *Drug Development and Industrial Pharmacy*, vol. 11, No. 4, pp. 891–900 (1985).

Helbig, J., et al. "Pharmaceutical oral dosage forms of an active agent capable of forming or releasing bicarbonate ions", *Pharmaceuticals*, (Abstract–98:221837d), vol. 98, p. 63 (1983).

*The Merck Index*, pp. 848–849, 9th Ed. (1976).

D.Q.M.Craig, "Polyethylene Glycols and Drug Release", *Drug Development and Industrial Pharmacy*, 16(17), pp. 2501–2526 (1990).

Remington's Pharmaceutical Sciences, 18th edition, Mack Publishing Company, 1990, pp 1634.*

* cited by examiner

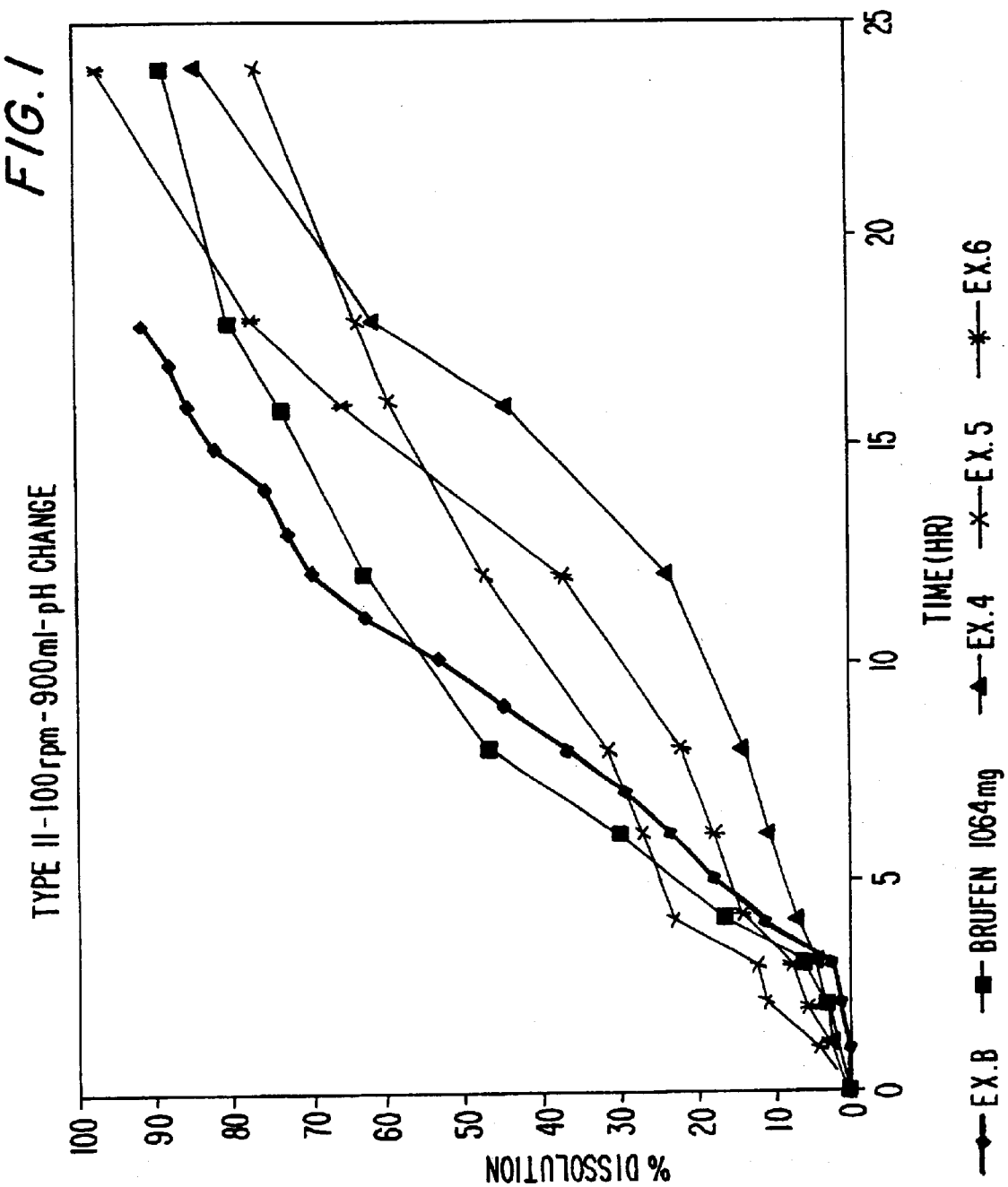

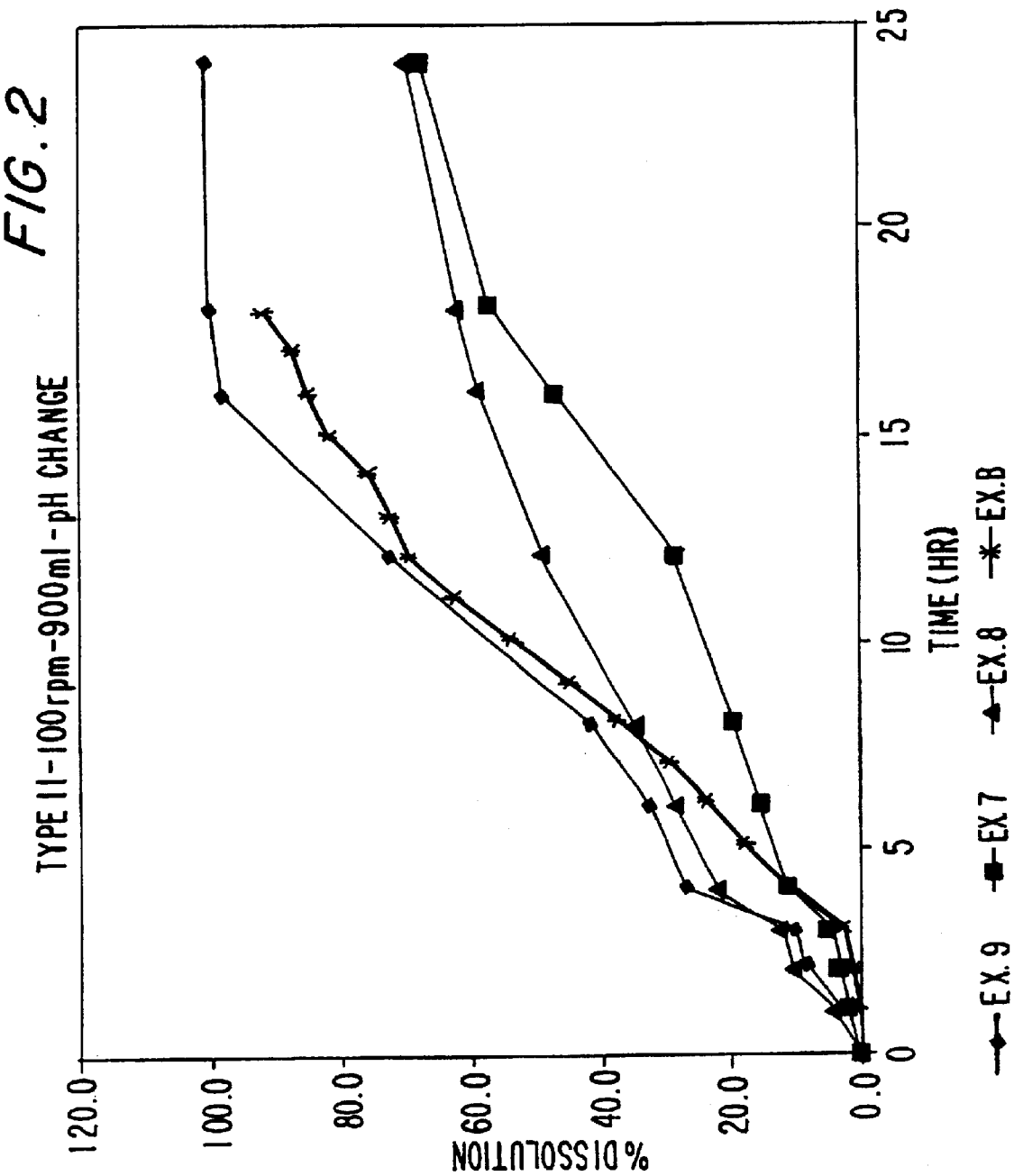

SUSTAINED RELEASE MATRIX FOR HIGH-DOSE INSOLUBLE DRUGS

This application is a continuation of U.S. patent application Ser. No. 08/889,424, filed Jul. 8, 1997, which claims the benefit of U.S. Provisional Application No. 60/021,335 filed Jul. 8, 1996.

BACKGROUND OF THE INVENTION

The advantages of controlled release products are well known in the pharmaceutical field and include the ability to maintain a desired blood level of a medicament over a comparatively longer period of time while increasing patient compliance by reducing the number of administrations necessary to achieve the same. These advantages have been attained by a wide variety of methods.

Oral controlled release delivery systems should ideally be adaptable so that release rates and profiles can be matched to physiological and chronotherapeutic requirements. While many oral controlled and sustained release formulations are already known, certain drugs that are relatively insoluble in water and which further have relatively high dose requirements (based on weight) present formulation difficulties which render them unsuitable for inclusion in sustained release formulations. Difficulties in preparing suitable sustained release formulations of insoluble drugs are increased when the dose of the insoluble drug to be delivered to render a therapeutic effect over the desired period of time is relatively high, e.g., 500 mg or greater.

An example of a high dose, insoluble drug is ibuprofen, which is a non-steroidal anti-inflammatory agent ("NSAID"). Several immediate release forms of ibuprofen are commercially available, e.g., Motrin® (available from Upjohn) and Brufen® (available from The Boots Company PLC), and a sustained release ibuprofen formulation, Brufen Retard™, is commercially available from the Boots Company PLC. Indoinethacin, another high dose insoluble NSAID, is commercially available in sustained release form as Indocin SR™ from Merck & Co., Inc.

There is still a need in the art for sustained release dosage forms of insoluble NSAIDs that are bioavailable and provide suitable release profiles of the NSAID from the dosage form over a sustained period of time, e.g. for about 12 to about 24 hours.

OBJECTS AND SUMMARY OF THE INVENTION

It is an object of the present invention to provide sustained release dosage forms of insoluble NSAIDs that provide an early onset of action and a sustained release of the NSAID.

It is a further object of the present invention to provide a method for preparing such bioavailable sustained release NSAID dosage forms.

It is a further object of the present invention to provide a sustained release excipient which is suitable for providing sustained release insoluble NSAID dosage forms.

The aforementioned objects and others are achieved by virtue of the present invention, which relates in part to a sustained release dosage form comprising from about 500 mg to about 1000 mg of an insoluble NSAID and an effective amount of a sustained release carrier to release the NSAID over a desired sustained period of time, which releases at least about 6 percent by weight of the NSAll) at about 2 hours and provides a $t_{50}$ (i.e., releases 50% by weight of the NSAID) at from about 12 to about 16 hours, after exposure of the dosage form to simulated gastrointestinal fluid.

The present invention is also directed to a sustained release oral dosage form containing ibuprofen as the active agent, which dosage form provides an early onset of action, e.g., the dosage form releases at least about 6 percent of the ibuprofen by weight about 2 hours, and/or the dosage form releases at least about 20 percent of the ibuprofen by weight about 4 hours, after exposure to simulated gastrointestinal conditions (such as via an in-vitro dissolution testing method), and which on the other hand provides a $t_{50}$ at about 12 to about 16 hours.

The present invention is also directed to an sustained release oral solid dosage form including from about 500 mg to about 1000 mg of an insoluble NSAID and a sustained release carrier, and which releases at least 20 percent by weight of the NSAID after about 4 hours and provides a $t_{50}$ at about 12 to about 16 hours, after exposure of the dosage form to simulated gastric fluid.

Sustained release dosage forms of NSAIDs according to the present invention have the desireable inventive advantage of providing a rapid onset of therapeutic effect of the insoluble NSAID and still provide sustained release of the NSAID so as to provide effective blood plasma levels of the ibuprofen over the entire dosing interval, e.g., about 24 hours. Such sustained release oral ibuprofen dosage forms provide an in-vitro dissolution rate, when measured, e.g., by the USP Dissolution Apparatus (Paddle Type II) of at least 6 percent by weight ibuprofen released after 2 hours, and/or at least about 20 percent by weight ibuprofen released after 4 hours, and which provides a $t_{50}$ after about 12 to about 16 hours.

In preferred embodiments, the insoluble NSAID is ibuprofen, which preferably comprises from about 500 mg to about 1000 mg of the dosage forms. A non-limiting list of other insoluble NSAIDs that may be used in accordance with the present invention include etodolac, fenoprofen (as the calcium salt), naproxen, mefenamic acid, nabumetone, tolmetin, and the like.

In other preferred embodiments, the sustained release carrier includes xanthan gum and a crosslinking agent, e.g., a galactomannan. In preferred embodiments, the sustained release carrier includes xanthan gum and locust bean gum in a 1:20 to about a 20:1 weight ratio. In preferred embodiments, the xanthan gum comprises from about 5 to about 95 percent by weight of the sustained release carrier. In other preferred embodiments, locust bean gum comprises from about 50 to about 95% by weight of the sustained release carrier.

In preferred embodiments, the dosage forms include from about 500 mg to about 1000 mg of the insoluble NSAID are suitable for dosing on a twice daily basis. In other preferred embodiments, the dosage forms include from about 500 mg to about 1000 mg of the insoluble NSAID and are suitable for dosing on a once daily basis. When administered on a once daily basis, it is preferred that more than one tablet containing 500 mg to 1000 mg of the insoluble NSAID are administered as a single dose to a patient.

In each of the embodiments set forth above, the dosage form is preferably a tablet.

The present invention is also directed to a method of preparing an oral sustained release dosage form of a high dose insoluble NSAID tablet comprising the steps of wet granulating a mixture of xanthan gum, locust bean gum, an inert diluent and insoluble NSAID to form a granulate; and tableting the resultant granulate into tablets containing from about 500 to about 1000 mg insoluble NSAID; wherein the ratio of the total weight of the insoluble NSAID in the tablet to the combined weight of xanthan gum and locust bean gum is from about 1:0.06 to about 1:0.4.

Another aspect of the invention is directed to a sustained release pharmaceutical excipient for use in sustained release oral solid dosage forms of insoluble NSAIDs, including xanthan gum, a crosslinking agent, and from about 20 to about 35 percent by weight of an inert diluent, e.g., dextrose.

In a preferred embodiment, the total combined weight of the xanthan gum and the crosslinking agent is from about 65 to about 80 percent of the excipient. In particularly preferred embodiments, the crosslinking agent is locust bean gum.

In another preferred embodiment of the invention, a sustained release ibuprofen tablet is provided comprising from about 500 to about 1000 mg ibuprofen, and from about 7 to about 40 percent of a hydrophilic gum matrix comprising xanthan gum and a cross-linking agent capable of cross-linking the xantlian gum when said tablet is exposed to an aqueous environment. In preferred embodiments, the cross-linking agent is, e.g., a homopolysaccharide such as locust bean gum, an ionizable gel strength enhancing agent, or mixtures thereof.

Yet another embodiment of the invention is directed to a sustained release tablet containing from about 500 mg to about 1000 mg of an insoluble NSAID in a sustained release matrix including xanthan gum and a crosslinking agent, wherein the total weight of the tablet is from about 110 percent to about 140 percent by weight of the insoluble NSAID, and the xanthan gum and the crosslinking agent comprise from about 7 to about 40 percent of the tablet by weight. In certain embodiments where the weight of NSAID, e.g., ibuprofen in the tablet is about 800 mg, the combined gum weight is from about 119 percent to about 136 percent of the insoluble NSAID.

The invention also provides a method of retarding the release of ibuprofen from a sustained release ibuprofen tablet containing xanthan gum when the tablet is exposed to an aqueous environment comprising replacing from about 5 to about 95 percent by weight of the xanthan gum in a sustained release ibuprofen tablet with a weight equivalent amount of a crosslinking agent, e.g., locust bean gum, wherein the ratio of said xanthan gum to said locust bean gum is from about 1:20 to about 20:1.

In embodiments where the cross-linking agent comprises an ionizable gel strength enhancing agent as defined herein, the ionizable gel strength enhancing agent may comprise from about 1 to about 20% of the total weight of sustained release carrier, e.g., xanthan gum, galactomannan gum and ionizable gel strength enhancing agent.

Yet another aspect of the invention is directed to a sustained release insoluble NSAID) tablet comprising from about 500 to about 1000 mg insoluble NSAID; xanthan gum; locust bean gum; and an inert diluent; wherein the combined weight of the xanthan gum and the locust bean gum is from about 7 to about 40 percent by weight of the final tablet weight and the ratio of insoluble NSAID to the combined weight of the xanthan gum and the locust bean gum is from about 1:0.08 to about 1:0.25. In preferred embodiments where the sustained release formulation is dosed on a twice-a-day basis, the tablet releases at least 6% by weight at about 2 hours after exposure of the dosage form to simulated gastrointestinal fluid and releases 50% by weight of the insoluble from about 5 to about 8 hours after such exposure. In other preferred embodiments, the sustained release ibuprofen tablet releases at least 20% at about 4 hours after exposure of the dosage form to simulated gastrointestinal fluid and releases 50% by weight of the insoluble NSAID at between from about 12 to about 16 hours after said exposure.

By "sustained release" it is meant for purposes of the present invention that the therapeutically active agent, e.g. a high dose insoluble drug such as ibuprofen, is released from the formulation at a controlled rate such that therapeutically beneficial blood levels (but below toxic levels) of the medicament are maintained over an extended period of time, e.g., providing a 12 hour or a 24 hour dosage form.

By "bioavailable" it is meant for purposes of the present invention that the therapeutically active agent, e.g. ibuprofen, is absorbed from the sustained release formulation and becomes available in the body at the intended site of drug action.

By "insoluble", it is meant that the therapeutically active medicament has an aqueous solubility of less than about 10 grams per liter (g/l).

The term "environmental fluid" is meant for purposes of the present invention to encompass, e.g., an aqueous solution such as in-vitro dissolution media, or gastrointestinal fluid.

The term "insoluble NSAID" for purposes of the present invention includes insoluble NSAID, pharmaceutically acceptable salts, complexes, esters, pharmaceutically acceptable isomers thereof, and crystalline forms thereof; with the caveat that the particular form of insoluble NSAID is insoluble as defined herein. All documents cited in this specification are hereby incorporated by reference in their entireties.

The term "high dose" for purposes of the present invention, when referring to an insoluble NSAID, refers to a total daily dose of NSAID. When referring to a dosage form or a formulation, the term "high dose" mean that the dosage form or formulation contains from about 500 mg to about 1000 mg of the insoluble NSAID.

BRIEF DESCRIPTION OF THE DRAWINGS

FIG. 1 is a graphical representation of the dissolution profiles for sustained release ibuprofen tablets prepared according to Examples 4, 5 and 6, Brufen Retard™ 800 mg tablet (available from The Boots Company PLC) and the ibuprofen formulation set forth in Example 1 of EP 234 670 A2; and FIG. 2 is a graphical representation of the dissolution profiles for sustained release ibuprofen tablets prepared according to Examples 7, 8 and 9, and the ibuprofen formulation set forth in Example 1 of EP 234 670 A2.

DETAILED DESCRIPTION

Non-steroidal anti-inflammatory drugs exhibits analgesic, anti-inflammatory and antipyretic activity. They are used to treat a variety of diseases and conditions, e.g., rheumatoid arthritis, inflammation.

Ibuprofen (α-methyl-4-(2-methylpropyl) benzene acetic acid) is a frequently prescribed NSAID. Typically, ibuprofen is administered in immediate-release form in adult doses ranging from 200 mg to 800 mg three or four times daily, i.e., about 600 mg to about 3200 mg ibuprofen/day. Ibuprofen is often used in chronic treatment regimens, and sustained release dosage forms are desirable to, e.g., reduce the number of necessary daily doses and to increase patient compliance. Ibuprofen, is practically insoluble in water and, as noted above, is a high dose drug, characteristics that present substantial challenges to even the skilled pharmaceutical formulator, especially when sustained release dosage forms of a particular NSAID are desired.

U.S. Pat. Nos. 4,994,276; 5,128,143; 5,135,757; 5,554,387; 5,512,297; 5,478,574; 5,472,711; 5,399,362; 5,399,359; 5,399,358 and 5,169,639, all assigned to the Assignee of the instant invention, describe sustained release pharmaceutical formulations and sustained release excipients suitable for use in sustained release dosage forms comprising a gelling agent of both hetero- and homo-polysaccharides which exhibit synergism, e.g., the combination of two or more polysaccharide gums produce a higher viscosity and faster hydration than that which would be expected by either of the gums alone, the resultant gel being faster-forming and more rigid. U.S. Pat. No. 5,455,046, also assigned to the Assignee of the present invention, discloses sustained release heterodisperse hydrogel systems for insoluble drugs. Suitable formulations according to the '046 patent including a gelling agent, an inert pharmaceutical diluent, a cationic cross-linking agent (e.g. calcium sulfate) and a medicament having moderate; to poor solubility, e.g., less than 10 g/l. All of the aforementioned references and all references cited herein are incorporated by references in their entireties.

Attempts have been made in the art to provide pharmaceutically acceptable sustained release ibuprofen formulations. European Patent Application Publication No. 0 234 670 A2 and its United States counterpart, U.S. Pat. No. 5,415,871 incorporated by reference, (both of which are assigned to The Boots Company PLC, Nottingham, England), describe solid sustained release pharmaceutical formulations comprising a compressed mixture of a pharmacologically active ingredient, e.g. ibuprofen, and 7.5 to 28% by weight of the formulation of a sustained release carrier comprising a major proportion of xanthan gum. The formulations purportedly require lower levels of sustained release carrier than previously suggested in the art and yet still provide release of the active agent into the body over a prolonged period. The formulations described therein are said to be suitable for once or twice daily administration to a patient.

The Examples in both the EP Publication '670 and the U.S. '871 patent suggest that to provide a suitable sustained release ibuprofen formulation it is preferred that xanthan gum is included as the only gum in the sustained release carrier. The Examples in these documents show that when a portion of the xanthan gum is replaced with another gum, e.g. sodium alginate, the rate of ibuprofen release from the dosage form is increased (compare, e.g. Examples 7 (15 % xanthan gum) and 11 (10% xanthan gum and 5% sodium alginate). Dissolution data provided for the sustained release ibuprofen formulation indicate that the $t_{50}$ for the exemplified sustained release ibuprofen formulations ranges from 3.5 to 9.5 hours and that the formulations release from 0.6 to 2.7 hours.

In contrast, preferred sustained release insoluble NSAID dosage forms of, e.g., according to ibuprofen, the present invention release at least 6% of the insoluble NSAID by weight at about 2 hours after exposure of the dosage form to simulated gastro-intestinal fluid and yet provide a prolonged and sustained release of ibuprofen from the dosage form as evidenced by a $t_{50}$ of from about 12 to about 16 hours. The unique dissolution profile provides a rapid onset of action coupled with an extended, release of insoluble NSAID from the dosage form. Preferably, the dosage form is suitable for dosing on a twice daily or once daily basis. When administered on a once-a-day basis, it is preferred that two or more dosage forms, e.g., tablets, are administered as a single dose.

It has been suggested that the unique dissolution profile, e.g. the initial release of ibuprofen at only 2 hours after in-vitro and the much slower prolonged release of the remaining ibuprofen is caused by the "swelling" and "gelling" properties of the xanthan gum and the cross-linking agent upon exposure to an environmental fluid. It is hypothesized that upon contact with an environmental fluid, the sustained release insoluble NSAID formulations prepared according to the present invention swell and gel to form a hydrophilic gel matrix from which the drug is released. The initial relatively faster release rate during the two hour period after exposure of the dosage form to environmental fluid. It is suggested that during the initial time period of exposure to an environmental fluid, the xanthan gum hydrates and form a gel matrix causing release of the active agent. As hydration continues, cross-linking of the xanthan gum occurs due to interaction with the cross-linking agent, causing an increase in gel strength and a decrease. in the rate of release of drug from the dosage form. This explanation is for discussion only, and is in no way intended to limit the scope of the present invention.

Xantban gum, the preferred heteropolysaccharide, is produced by microorganisms, for instance, by fermentation with the organism xaiithomonas compestris. Most preferred is xanthan gum which is a high molecular weight ($>10^6$) heteropolysaccharide. Xanthan gum contains D-glucose, D-mannose, D-glucuronate in the molar ratio of 2.8:2.0:20, and is partially acetylated with about 4.7% acetyl. Xanthan gum also includes about 3% pyruvate, which is attached to a single unit D-glucopyromosyl side chain as a metal. It dissolves in hot or cold water and the viscosity of aqueous solutions of xanthan gum is only slightly affected by changes in the pH of a solution between 1 and 11.

The term "heteropolysaccharide" as used in the present invention is defined as a water-soluble polysaccharide containing two or more kinds of sugar units, the heteropolysaccharide having a branched or helical configuration, and having excellent water-wicking properties and immense thickening properties. When admixed with an appropriate ionizable gel strength enhancing agent capable of enhancing the gel strength of the hydrophilic matrix upon exposure to an aqueous solution, e.g. gastric fluid, etc., the gum packs closely and many intermolecular attachments are formed which make the structure strong and provide a hydrophilic gum matrix having high gel strength. The ionizable gel strength enhancing agent is therefore an agent capable of enhancing the gel strength of a gel formed by exposure of the lieteropolysaccliaride to an aqueous environment, thus affecting the rate of release of the active medicament.

The galactomannans used in the present invention which are capable of cross-inking with the xanthan gum are polysaccharides which are composed solely of mannose and galactose. Galactomannans which have higher proportions of unsubstituted mannose regions have been found to achieve more interaction with the heteropolysaccharide. Locust bean gum, which has a higher ratio of mannose to the galactose, is especially preferred as compared to other galactomannans such as guar and hydroxypropyl guar.

The cross-linking agent may be, e.g., a galactomannan such as locust bean gum or an ionizable gel strength enhancing agent. The ionizable gel strength enhancing agent may be monovalent, divalent or multivalent ionizable salts. Preferred salts are the inorganic salts, including various alkali metal and/or alkaline earth metal sulfates, chlorides, borates, bromides, etc. Ionizable alkaline earth organic salts such as citrates, acetates, lactates, etc. may also be used in accordance with the present invention. Specific examples of suitable ionizable gel strength enhancing agents include calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate, alkali metal chlorides, magnesium chloride, calcium chloride, organic acids such as citric, succinic, fumaric, malic, maleic, glutaric, lactic and the like, alkali metal sulfates such as sodium sulfate, alkali metal alkyl sulfates wherein the alkyl group is from 1 to 14 carbon atoms, such as sodium methyl sulfate, sodium lauryl sulfate and the like as well as dioctyl sodium sulfosuccinate, dihydrogen sodium phosphate, monohydrogen sodium phosphate, disodium hydrogen phosphate, sodium chloride, sodium fluoride and mixtures thereof. Multivalent metal cations may also be utilized. However, the preferred ionizable gel strength enhancing agents are bivalent. Particularly preferred salts are calcium sulfate and sodium chloride.

It is to be understood that the ionizable compound may be a single compound or a mixture of two or more materials that provide the desired release characteristics. The ionizable gel strength enhancing agents of the present invention are added in an amount effective to obtain a desirable increased gel strength of a gel formed by exposure of the heteropoly-saccharide to an aqueous environment.

In other embodiments of the invention, the ionizable gel enhancing agent may comprise a surfactant or wetting agent such as pharmaceutically acceptable anionic surfactants, cationic surfactants, amphoteric (amphipathic/amphophilic) surfactants, and non-ionic surfactants. Examples of suitable surfactant or wetting agents include alkali metal chlorides, magnesium chloride, calcium chloride, organic acids such as citric, succinic, fumaric, malic, maleic, glutaric, lactic and the like, alkali metal sulfates such as sodium sulfate, alkali metal alkyl sulfates wherein the alkyl group is from 1 to 14 carbon atoms, such as sodium methyl sulfate, sodium lauryl sulfate and the like as well as dioctyl sodium sulfosuccinate, dihydrogen sodium phosphate, monohydrogen sodium phosphate, disodium hydrogen phosphate, sodium chloride, sodium fluoride and mixtures thereof. It is to be understood that the ionizable compound may. be a single compound or a mixture of two or more materials that provide the desired release characteristics. Other examples of suitable surfactants and/or suitable wetting agents are disclosed in U.S. Pat. No. 5,478,574, assigned to the assignee of the present invention.

The controlled release properties of the controlled release formulations of the present invention may be optimized when xanthan gum comprises from about 1 to 99% by weight of the sustained release carrier. In where the sustained release carrier comprises a crosslinking preferably comprises from about 1 to about 99% by weight of the sustained release carrier. In embodiments where the crosslinking agent is a galactomannan, e.g., locust bean gum, xantlian gum preferably comprises from about 5 to 95% by weight of the sustained release carrier. In other embodiments where the crosslinking agent is an ionizable gel strength enhancing agent, e.g., calcium sulfate, the ionizable gel strength enhancing agent comprises from about 1 to about 20% by weight of the sustained release carrier. Combinations of crosslinking agents, e.g., a galactomannan and an ionizable gel strength enhancing agents may also be included in the sustained release carrier. The skilled artisan will understand that the above ratios will vary according to, e.g., the type of crosslinking agent or combinations of crosslinking agents present in the formulation, so long as the desired dissolution parameters of the dosage form is maintained.

Other acceptable gelling agents may optionally be included in sustained release formulations of the present invention include those gelling agents well-known in the art. Examples include vegetable gums such as alginates, carrageenan, pectin, guar gum, xanthan gum, modified starch, hydroxypropylmethylcellulose, methylcellulose, and other cellulosic materials such as sodium carboxymethylcellulose and hydroxypropyl cellulose. This list is not meant to be exclusive.

The formulations of the present invention also include an inert diluent. Any generally accepted soluble or insoluble inert diluent material can be used. Preferably, the inert diluent comprises a monosaccharide, a disaccharide, a polyhydric alcohol, a cellulose (such as microcrystalline cellulose), starches, and/or mixtures thereof Examples of suitable inert pharmaceutical fillers include sucrose, dextrose, lactose, microcrystalline cellulose, xylitol, fructose, sorbitol, mixtures thereof and the like. However, it is preferred that a soluble pharmaceutical filler such as dextrose, sucrose, or mixtures thereof be used.

Examples of such pre-manufactured direct compression excipients include Emcocel® (microcrystalline cellulose, N.F.), Emdex® (dextrates, N.F.), and Tab-Fine® (a number of direct-compression sugars including sucrose, fructose, and dextrose), all of which are commercially available from Edward Mendell Co., Inc., Patterson, N.Y.). Other direct compression diluents include Anhydrous lactose (Lactose N.F., anhydrous direct tableting) from Sheffield Chemical, Union, N.J. 07083; Elcems® G-250 (Powdered cellulose, N.F.) from Degussa, D-600 Frankfurt (Main) Germany; Fast-Flo Lactose® (Lactose, N.F., spray dried) from Foremost Whey Products, Banaboo, Wis. 53913; Maltrin® (Agglomerated maltrodextrin) from Grain Processing Corp., Muscatine, Iowa 52761; Neosorb 60® (Sorbitol, N.F., direct-compression) from Roquette Corp., 645 5th Ave., New York, N.Y. 10022; Nu-Tab® (Compressible sugar, N.F.) from Ingredient Technology, Inc., Pennsauken, N.J. 08110; Poly-plasdone XL® (Crospovidone, N.F., cross-linked polyvinylpyrrolidone) from GAF Corp., New York, N.Y. 10020; Primojel® (Sodium starch glycolate, N.F., carboxymethyl starch) from Generichem Corp., Little Falls, N.J. 07424; Solka Floc® (Cellulose floc) from Edward Mendell Co., Carmel, N.Y. 10512; Spray-dried lactose® (Lactose N.F., spray dried) from Foremost Whey Products, Baraboo, Wis. 53913 and DMV Corp., Vehgel, Holland; and Sta-Rx 1500® (Starch 1500) (Pregelatinized starch, N.F., compressible) from Colorcon, Inc., West Poiiit, Pa. 19486. Pre-manufactured directed compression excipients may also comprise all or a portion of the inert diluent.

In further alternative embodiments of the invention, a therapeutically active agent can be incorporated (admixed, granulated, etc.) with any of the ingredients of the sustained release excipient, if so desired. The remaining formulation steps would remain essentially the same as would be understood by one skilled in the art.

In further embodiments of the present invention, the inert diluent which is used in conjunction with the sustained release pharmaceutical excipient of the present invention is an augmented microcrystalline cellulose as disclosed in U.S. patent application Ser. No. 5,585,115 entitled "PHARMACEUTICAL EXCIPIENT HAVING IMPROVED COMPRESSIBILITY", inventors B. Sherwood, J. Staniforth and E. Hunter, hereby incorporated by reference.

In certain embodiments of the invention, the sustained release carrier also includes a hydrophobic material in an amount effective to slow the hydration of the gum without disrupting the hydrophilic matrix formed by the heteropolysaccharide when the formulation is exposed to fluids in an environment of use. This may be accomplished by granulating the sustained release carrier with a solution or dispersion of hydrophobic material prior to the incorporation of the medicament. The hydrophobic material may be selected from alkylcelluloses, acrylic and/or methacrylic acid polymers or copolymers, hydrogenated vegetable oils, zein, as well as other pharmaceutically acceptable hydrophobic materials known to those skilled in the art. A preferred hydrophobic cellulosic material is ethylcellulose. The amount of hydrophobic material incorporated into the sustained release matrix is that which is effective to slow the hydration of the gums without disrupting the hydrophilic matrix formed upon exposure to an environmental fluid, e.g. a gastric fluid.

In certain embodiments of the present invention, the hydrophobic material may be included in the sustained release carrier in an amount from about 1% to about 20% by weight. More preferably, the hydrophobic material may be included in the sustained release matrix in an amount from about 3% to about 12%, and most preferably from about 5% to about 10%, by weight of the final formulation. The hydrophobic material may be dissolved in an organic solvent or dispersed in an aqueous solution for incorporation into the formulation.

The combination of the xanthan gum with the cross-linking agent and inert diluent provides a ready to use sustained release excipient in which a formulator need only blend the desired active medicament and an optional lubricant with the excipient and then make an oral solid dosage form. The sustained release excipient may thus comprise a physical admix of the xanthan gum with the cross-linking agent and inert diluent.

The sustained release pharmaceutical excipient prepared in accordance with the present invention is preferably wet granulated prior to addition of the medicament. In this technique, the desired amounts of the xanthan gum cross-linking agent, and inert diluent are mixed together and moistened with a wet granulating aid such as water, propylene glycol, glycerol, alcohol or the like is added to prepare a moistened mass. The moistened mass is dried, and then milled with, e.g., conventional equipment, into granules. The resultant sustained release excipient is ready to use. The sustained release excipient has certain advantages including it is free-flowing, good cohesive properties, and can be directly admixed with the insoluble NSAID, e.g., via wet granulation, formed into the desired dosage form such as a tablet. On the other hand, the granulate can be formulated into a capsule, used in the granulate form, extruded, and/or spheronized with an active medicament to form pellets, etc. In alternative preferred embodiments, the individual ingredients of the sustained release excipient may be wet granulated with all or part of the insoluble NSAID.

In a preferred embodiment of the invention, sustained release ibuprofen tablets are prepared by wet granulating together the requisite amounts of ibuprofen, crosslinking agent (e.g. locust bean gum) and inert diluent in the presence of a wet granulating aid, e.g. water or ethyl alcohol. The resultant mixture may then be dried, e.g. in a fluid bed dryer, and compressed into tablets.

Optionally, lubricants such as those described above may be mixed with the granulation prior to tableting. Other tableting or processing aids may be added as required.

The dosage forms of the present invention are preferably tablets. However, as noted above, the ingredients may also be formulated in a capsule, extruded and spheronized with an active medicament to form pellets, etc.

For example, the complete mixture, in an amount sufficient to make a uniform batch of tablets, is subjected to tableting in a conventional production scale tableting machine at normal compression pressure, i.e. about 2000–1600 lbs/sq in. However, the mixture should not be compressed to such a degree that there is subsequent difficulty in its hydration when exposed to gastric fluid. An effective amount of any generally accepted pharmaceutical lubricant, including the calcium or magnesium soaps may be added to the above-mentioned ingredients of the excipient be added at the time the medicament is added, or in any event prior to compression into a said dosage form. One preferred lubricant is Pruv®, e.g., in the amount of about 3.0 percent of the solid dosage form.

The tablets may be optionally coated with an overcoat containing, e.g., hydroxypropylmethylcellulose, colorants and the like.

In preferred embodiments of the invention where the NSAID is ibuprofen and the crosslinking agent is locust bean gum, the weight ratio of ibuprofen to the combined weight of the gums, i.e. xanthan gum and locust bean gum, is from about 1:0.06 to about 1:0.4, and preferably from about 1:0.08 to about 1:0.25. The ibuprofen:gum ratio is indicative of the reduced amount of gum required compared to prior art sustained release ibuprofen formulations. The dosage forms of the present invention are economically advantageous in that less gum is required to produce a suitable dosage form, with the added advantages of smaller tablet size and once or twice daily dosing.

Variables which may affect the release rate and the compressibility of tablets prepared with the excipient of the present invention are the drug to gum ratio; the method of incorporation of excipient (method of granulation); the relative amount of the gum to ionizable gel strength enhancing agent; and the ratio of active medicament to the sustained release excipient.

An effective amount of a wetting agent may be included in the formulation in order to increase the bioavailability of the ibuprofen. The wetting agent may be added, e.g., by spraying while mixing the granulate.

Suitable wetting agents for use in conjunction with the present invention include polyethyleneglycols as esters or ethers. Examples include polyethoxylated castor oil, polyethoxylated hydrogenated castor oil, polyethoxylated fatty acid from castor oil or polyethoxylated fatty acid from castor oil or polyethoxylated fatty acid from hydrogenated castor oil. Commercially available wetting agents which can be used are known under trade names Cremophor, Myrj, Polyoxyl 40 stearate, Emerest 2675, Lipal 395 and PEG 3350. An especially preferred wetting agent is polyethyleneglycol having a molecular weight of 3,350 (i.e., PEG 3350).

When included in the formulation, the wetting agent is dissolved in a suitable solvent such as water, and is thereafter added to the blended mixture of the sustained release excipient and the medicament. This allows the wetting agent to wet the particles of the excipient such that when the solvent evaporates the particles of the medicament which precipitate are tiny and do not aggregate. A granulate of the medicament and the wetting agent is obtained which is preferably finely and homogeneously dispersed in the excipient.

The wetting agent is preferably included in an amount effective to provide a final sustained release product having acceptable bioavailability. For example, in certain embodiments of the present invention wherein the medicament is ibuprofen, the wetting agent is included in an amount from about 5% to about 10% of the final product, by weight.

In certain embodiments of the embodiment a hydrophobic polymer such as those described hereinabove is added to the mixture of wetting agent and ibuprofen.

The hydrophobic material may be dissolved in an organic solvent or dispersed in an aqueous solution. Thereafter, the hydrophobic material may be used to coat the granulate of ibuprofen/wetting agent/sustained release excipient. The granulate may be coated with the hydrophobic coating to a weight gain of, e.g., from about 1 to about 20 percent, and preferably from about 5 to about 10 percent. The granulation is then preferably dried. Thereafter, the granulate may be further formulated into an appropriate oral dosage form, for example, by compression of the resulting granulate into appropriately sized tablets, by filling gelatin capsules with an appropriate amount of the granulate (with or without compression of the granulate), as well as use in the manufacture of other oral dosage forms known to those skilled in the art. This embodiment may be particularly beneficial to control the amount of ibuprofen released during the initial phases of dissolution when the formulation is exposed to fluid in an environment of use, e.g., in-vitro dissolution or in the gastrointestinal tract.

In certain embodiments of the present invention, the tablet core includes a portion of the total dose of the insoluble NSAID or an additional dose of the insoluble NSAID in either the hydrophobic or enteric coating, or in an additional overcoating coated on the outer surface of the tablet core (without the hydrophobic or enteric coating) or as a second coating layer coated on the surface of the base coating comprising the hydrophobic or enteric coating material. This may be desired when, for example, a loading dose of ibuprofen is needed to provide therapeutically effective blood levels of the active agent when the formulation is first exposed to gastric fluid. The loading dose of medicament included in the coating layer may be, e.g., from about 10% to about 40% of the total amount of medicament included in the formulation. It is particularly preferred to include all or a portion of the total dose of the insoluble NSAID as a coating around the tablet core when the sustained release carrier comprises from about 40 to about 100% by weight xanthan gum, e.g. from about 45 to about 99% by weight. In such embodiments, it is preferable that the dosage form and/or the tablet core is coated with a sustained and/or release coating an enteric coating containing a hydrophobic polymer.

DETAILED DESCRIPTION OF THE PREFERRED EMBODIMENTS

The following examples illustrate various aspects of the present invention. They are not to be construed to limit the claims in any manner whatsoever.

EXAMPLES 1–3

In Examples 1–3, a sustained release excipient is prepared as set forth below:

TABLE 1

| Preparation of a Sustained Release Excipient | | | |
|---|---|---|---|
| Component (%) | Ex. 1 | Ex. 2 | Ex. 3 |
| Xanthan Gum | 35 | 5 | 65 |
| Locust Bean Gum | 35 | 65 | 5 |
| Dextrose | 30 | 30 | 30 |
| Water* | 28% | 37% | 21% |

Processing Steps: 1.5 kg batch
1. Weigh out xanthan gum, locust bean gum and dextrose.
2. Charge high shear mixer/granulator with xanthan gum, locust bean gum and dextrose and dry blend for 3 minutes.
3. Add water and granulate until desirable granules are formed.
4. Dry granules in fluid bed dryer at 70° C. until LOD is less than 5%.
5. Pass granules through Fitzmill @3500 rpm, hammers forward.

EXAMPLES 4–9 Preparation of Tablets

The sustained release excipients prepared in Examples 4–6 are mixed with the drug (ibuprofen) and sustained release ibuprofen tablets are prepared as set forth below:

TABLE 2

| Tablets of Examples 4–6 | | | |
|---|---|---|---|
| Component (%) | Ex. 4 | Ex. 5 | Ex. 6 |
| Sustained release excipient | 280 | 280 | 280 |
| Ibuprofen | 800 | 800 | 800 |
| Mg Stearate | 10 | 10 | 10 |

Processing Steps: 1.5 kg batch
1. Screen drug through 25 mesh.
2. Weigh out sustained release excipient and drug.
3. Charge high shear mixer/granulator with sustained release excipient and drug and dry blend for 3 minutes.
4. Add water while mixing and granulate until desirable granules are formed.
5. Pass granules through Fitzmill @2500 rpm, blades forward.
6. Dry granules in fluid bed dryer at 55° C. until LOD is less than 3%.
7. Pass granules through 16 mesh screen on an oscillating granulator.
8. Using a V-Blender, blend granules and Magnesium Stearate for 5 minutes.
9. Compress into tablets using 0.3750×0.8300 in. capsule shaped punches to a hardness of about 15 kP.

*Water is removed during precesing

The final composition of the tablets of Examples 4–6 are set forth in Tables 3–5 below:

TABLE 3

| Tablet Composition of Example 4 | | |
|---|---|---|
| Component (%) | mg/Tablet | % |
| Excipient (Ex. 1) | 280 | 25.7 |
| (Xanthan Gum) | (98) | (9.0) |
| (Locust Bean Gum) | (98) | (9.0) |
| (Dextrose) | (84) | (7.7) |
| Ibuprofen | 800 | 73.3 |
| Mg Stearate | 10 | 1 |
| Total | 1090 | 100.0 |

TABLE 4

| Tablet Composition of Example 5 | | |
|---|---|---|
| Component (%) | mg/Tablet | % |
| Excipient (Ex. 2) | 280 | 25.7 |
| (Xanthan Gum) | (14) | (1.3) |

TABLE 4-continued

Tablet Composition of Example 5

| Component (%) | mg/Tablet | % |
|---|---|---|
| (Locust Bean Gum) | (182) | (16.7) |
| (Dextrose) | (84) | (7.7) |
| Ibuprofen | 800 | 73.3 |
| Mg Stearate | 10 | 1 |
| Total | 1090 | 100.0 |

TABLE 5

Tablet Composition of Example 6

| Component (%) | mg/Tablet | % |
|---|---|---|
| Excipient (Ex. 3) | 280 | 25.7 |
| (Xanthan Gum) | (14) | (16.7) |
| (Locust Bean Gum) | (182) | (1.3) |
| (Dextrose) | (84) | (7.7) |
| Ibuprofen | 800 | 73.3 |
| Mg Stearate | 10 | 1 |
| Total | 1090 | 100.0 |

EXAMPLES 7–9

Sustained release ibuprofen tablets are prepared in accordance using the excipients of Examples 1–3 using the process described in Examples 4–6 except that the total amount of excipient in the tablet was reduced from 280 mg to 140 mg. The composition of the tablets according to Examples 7–9 are set forth in Tables 6–8 below:

TABLE 6

Tablet Composition of Example 7

| Component (%) | mg/Tablet | % |
|---|---|---|
| Sustained release excipient | 140 | 14.7 |
| (Xanthan Gum) | (49) | (5.2) |
| (Locust Bean Gum) | (49) | (5.2) |
| (Dextrose) | (42) | (4.4) |
| Ibuprofen | 800 | 84.2 |
| Mg Stearate | 10 | 1.1 |
| Total | 950 | 100.0 |

TABLE 7

Tablet Composition of Example 8

| Component (%) | mg/Tablet | % |
|---|---|---|
| Sustained release excipient | 140 | 14.7 |
| (Xanthan Gum) | (7) | (0.7) |
| (Locust Bean Gum) | (91) | (9.6) |
| (Dextrose) | (42) | (4.4) |
| Ibuprofen | 800 | 84.2 |
| Mg Stearate | 10 | 1.1 |
| Total | 950 | 100.0 |

TABLE 8

Tablet Composition of Example 9

| Component (%) | mg/Tablet | % |
|---|---|---|
| Sustained release excipient | 140 | 14.7 |
| (Xanthan Gum) | (91) | (9.6) |
| (Locust Bean Gum) | (7) | (0.7) |
| (Dextrose) | (42) | (4.4) |
| Ibuprofen | 800 | 84.2 |
| Mg Stearate | 10 | 1.1 |
| Total | 950 | 100.0 |

EXAMPLES 10–11—Dissolution Testing

EXAMPLE 10

Tablets prepared in accordance with Examples 4–6 are tested with respect to in-vitro dissolution. The dissolution tests are conducted in an automated USP dissolution apparatus (Paddle Type II), and the amount of drug released was analyzed via UV analysis. In Comparative Example A, Brufen Retard™, sustained release ibuprofen tablets commercially available from The Boots Company were also tested according to the same method. In Comparative Example B, the dissolution of Example 1 (a sustained release ibuprofen tablet) set forth in EP 234670 A2 is composed. Example 1 of EP 234670 is a sustained release ibuprofen tablet containing 800 mg ibuprofen, 196.9 mg xanthan gum (Keltrol F), 3.1 mg colloidal silicon dioxide (Aerosil 200) 25.9 mg polyvinylpyrrollidone (Plasdone K29–32) and 10.4 mg stearic acid. The dissolution of Example 1 of EP 234670 A2 was undertaken in accordance with the general procedures set forth herein, and the dissolution results are taken from the results provided in that publication.

TABLE 9

Dissolution Method

| Dissolution Results | Hours | pH |
|---|---|---|
| Type II | 0 | 2.5 |
| 900 ml | 1 | 4.5 |
| 100 rpm | 2 | 4.5 |
|  | 3 | 6.8 |
|  | 4–24 | 6.8 |

TABLE 10

Dissolution Results

| Time (Hr) | Ex. 4 | Ex. 5 | Ex. 6 | Ex. A | Ex. B |
|---|---|---|---|---|---|
| 0 | 0 | 0 | 0 | 0 | 0 |
| 1 | 2.4 | 4.1 | 2.3 | 1.3 | 0.2 |
| 2 | 3.2 | 11.0 | 5.8 | 3.1 | 1.1 |
| 3 | 4.4 | 12.4 | 7.7 | 5.9 | 2.5 |
| 4 | 6.9 | 22.7 | 14.2 | 16.3 | 11.4 |
| 6 | 10.4 | 26.7 | 17.5 | 29.9 | 23.3 |
| 8 | 14 | 31.4 | 21.8 | 46.5 | 36.5 |
| 12 | 23.8 | 47.3 | 37.3 | 62.8 | 69.3 |
| 16 | 44.5 | 59.6 | 65.5 | 73.3 | 85.2 |
| 18 | 61.2 | 63.3 | 77.2 | 79.8 | 91.5 |
| 24 | 84.3 | 76.8 | 87.2 | 88.1 |  |

The dissolution results are also graphically depicted in FIG. 1. The dissolution results indicate that the tablets of Examples 4–6 provide sustained release of the ibuprofen from the dosage form.

EXAMPLE 11

Dissolution tests are conducted on the tablets of Examples 7, 8 and 9 in accordance with the method described in Example 10 above. The results are set forth in Table 11 below:

TABLE 11

Dissolution Results

| Time (Hr) | Ex. 7 | Ex. 8 | Ex. 9 | Ex. A | Ex. B |
|---|---|---|---|---|---|
| 0 | 0 | 0 | 0 | 0 | 0 |
| 1 | 1.7 | 3.5 | 2.3 | 1.3 | 0.2 |
| 2 | 3.6 | 10.2 | 8.1 | 3.1 | 1.1 |
| 3 | 4.8 | 11.8 | 10.1 | 5.9 | 2.5 |
| 4 | 11.0 | 22.0 | 26.0 | 16.3 | 11.4 |
| 6 | 15.3 | 27.9 | 32.4 | 29.9 | 23.3 |
| 8 | 19.1 | 34.4 | 41.4 | 46.5 | 36.5 |
| 12 | 27.7 | 48.8 | 72.7 | 62.8 | 69.3 |
| 16 | 46.6 | 58.5 | 98.3 | 73.3 | 85.2 |
| 18 | 56.4 | 61.6 | 100.2 | 79.8 | 91.5 |
| 24 | 67.4 | 70.0 | 100.9 | 88.1 | |

The dissolution results are also graphically depicted in FIG. 2.

The results show that a suitable sustained release of ibuprofen is still obtained although the tablet formulations of Examples 7–9 contain 50% less sustained release excipient than Examples 4–6.

The Examples provided above are not meant to be exclusive. Many other variations of the present invention will be apparent to those skilled in the art, and are contemplated to be within the scope of the present invention.

What is claimed is:

1. A sustained release ibuprofen dosage form comprising a dose of about 500 mg to about 1000 mg ibuprofen; a tablet core comprising xanthan gum and a portion of said dose of ibuprofen; wherein from about 1 to about 20 percent by weight of a remaining portion of said dose is coated on said tablet core; said dosage form providing a dissolution of said NSAID in-vitro when measured by the USP Type II (Paddle) Method, of from about 6 percent by weight of said NSAID released after about 2 hours and a $t_{50}$ after about 12 to about 16 hours.

2. The sustained release ibuprofen tablet of claim 1, wherein said coating further includes a hydrophobic material.

3. The sustained release tablet of claim 1, wherein at least about 20 percent by weight of the ibuprofen is released in about 4 hours.

4. The sustained release tablet of claim 1, wherein the tablet provides blood plasma levels of ibuprofen for about 24 hours.

5. The sustained release tablet of claim 1, comprising from about 800 to about 1000 mg ibuprofen.

6. The sustained release tablet of claim 1, comprising a matrix in which the ibuprofen is uniformly dispersed with said xanthan gum.

7. The sustained release tablet of claim 1, comprising from about 1 to about 20 percent by weight of the ibuprofen as the coating.

8. The sustained release tablet of claim 1, further comprising a sustained release coating between said ibuprofen coating and said core.

* * * * *